(12) United States Patent
Yao et al.

(10) Patent No.: US 11,298,109 B2
(45) Date of Patent: Apr. 12, 2022

(54) ULTRASONIC DIAGNOSTIC APPARATUS AND IMAGE PROCESSING APPARATUS

(71) Applicant: Toshiba Medical Systems Corporation, Otawara (JP)

(72) Inventors: Cong Yao, Otawara (JP); Tetsuya Kawagishi, Nasushiobara (JP); Yoshitaka Mine, Nasushiobara (JP); Naoki Yoneyama, Otawara (JP); Hiroki Yoshiara, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 985 days.

(21) Appl. No.: 14/850,807

(22) Filed: Sep. 10, 2015

(65) Prior Publication Data

US 2016/0066888 A1  Mar. 10, 2016

Related U.S. Application Data

(63) Continuation of application No. PCT/JP2014/056072, filed on Mar. 7, 2014.

(30) Foreign Application Priority Data

Mar. 11, 2013  (JP)  .............................. JP2013-048394

(51) Int. Cl.
*A61B 8/08* (2006.01)
*G01S 7/52* (2006.01)
(Continued)

(52) U.S. Cl.
CPC ................ *A61B 8/481* (2013.01); *A61B 8/06* (2013.01); *A61B 8/463* (2013.01); *A61B 8/5223* (2013.01);
(Continued)

(58) Field of Classification Search
CPC ........... A61B 8/00; A61B 8/481; A61B 8/463; A61B 8/5223; A61B 8/06; A61B 8/5246; G01S 7/52038
See application file for complete search history.

(56) References Cited

U.S. PATENT DOCUMENTS

5,575,286 A * 11/1996 Weng ................... A61B 8/0866
600/425
5,971,927 A * 10/1999 Mine ........................ A61B 8/06
600/455
(Continued)

FOREIGN PATENT DOCUMENTS

CN  1917814 A  2/2007
CN  1943516 A  4/2007
(Continued)

OTHER PUBLICATIONS

Combined Office Action and Search Report dated Dec. 29, 2016 in Chinese Patent Application No. 201480013750.0 (with English translation of category of cited documents).
(Continued)

*Primary Examiner* — Sean D Mattson
(74) *Attorney, Agent, or Firm* — Oblon, McClelland, Maier & Neustadt, L.L.P.

(57) ABSTRACT

An ultrasonic diagnostic apparatus according to an embodiment includes a candidate-position extracting circuitry and a position setting circuitry. The candidate-position extracting circuitry extracts a first position through comparison of a fundamental wave component between a plurality pieces of image data collected by performing ultrasonic scanning on a subject injected with a contrast agent. The candidate-position extracting circuitry also extracts a second position through comparison of a harmonic component between the pieces of image data. The position setting circuitry sets the first position or the second position as a position of a region (Continued)

of interest where predetermined analysis is performed in at least one image data of the pieces of image data.

9 Claims, 10 Drawing Sheets

(51) Int. Cl.
  *A61B 8/06* (2006.01)
  *A61B 8/00* (2006.01)
(52) U.S. Cl.
  CPC ......... *G01S 7/52038* (2013.01); *A61B 8/5246* (2013.01)

(56) References Cited

U.S. PATENT DOCUMENTS

| | | | |
|---|---|---|---|
| 6,193,660 B1* | 2/2001 | Jackson | A61B 8/00 600/443 |
| 6,368,277 B1* | 4/2002 | Mao | A61B 8/08 600/441 |
| 2002/0128555 A1* | 9/2002 | Maxwell | A61B 8/54 600/447 |
| 2006/0173312 A1* | 8/2006 | Jackson | A61B 8/00 600/437 |
| 2007/0016016 A1 | 1/2007 | Haras et al. | |
| 2007/0032726 A1* | 2/2007 | Osaka | A61B 5/0048 600/459 |
| 2007/0055158 A1* | 3/2007 | Jackson | A61B 5/11 600/443 |
| 2007/0073146 A1 | 3/2007 | Phillips et al. | |
| 2010/0069756 A1* | 3/2010 | Ogasawara | A61B 8/08 600/447 |
| 2011/0208061 A1* | 8/2011 | Chang | A61B 8/0833 600/458 |
| 2011/0243401 A1* | 10/2011 | Zabair | G06K 9/00 382/128 |
| 2011/0301466 A1* | 12/2011 | Wang | A61B 8/06 600/454 |
| 2013/0090557 A1* | 4/2013 | Takagi | A61B 8/085 600/431 |

FOREIGN PATENT DOCUMENTS

| | | |
|---|---|---|
| JP | 07-178095 A | 7/1995 |
| JP | 2006-334404 A | 12/2006 |
| JP | 2007-007193 A | 1/2007 |
| JP | 2007-090075 A | 4/2007 |
| JP | 2007-330764 A | 12/2007 |
| WO | WO 2012/137431 A1 | 10/2012 |

OTHER PUBLICATIONS

International Search Report dated Apr. 8, 2014 for PCT/JP2014/056072 filed Mar. 7, 2014 with English Translation.
International Written Opinion dated Apr. 8, 2014 for PCT/JP2014/056072 filed Mar. 7, 2014.

* cited by examiner

| FRAME | CENTER OF REGION OF INTEREST | SIZE OF REGION OF INTEREST | FLAG |
|---|---|---|---|
| 1 | | | |
| 2 | (6, 7)=(5, 5)+(1, 2) | 2 cm | - |
| 3 | (5, 5) | 2 cm | - |
| 4 | | | |
| 5 | | | |
| . | | | |
| . | | | |
| . | | | |
| n | | | |

ULTRASONIC DIAGNOSTIC APPARATUS AND IMAGE PROCESSING APPARATUS

CROSS-REFERENCE TO RELATED APPLICATIONS

This application is a continuation of PCT international application Ser. No. PCT/JP2014/056072 filed on Mar. 7, 2014 which designates the United States, incorporated herein by reference, and which claims the benefit of priority from Japanese Patent Application No. 2013-048394, filed on Mar. 11, 2013, the entire contents of which are incorporated herein by reference.

FIELD

Embodiments described herein relate generally to an ultrasonic diagnostic apparatus and an image processing apparatus.

BACKGROUND

In recent years, an intravenous ultrasound contrast agent has been commercialized and a "contrast echo method" has been performed. Hereinafter, the ultrasound contrast agent may sometimes be described as a contrast agent for short. The purpose of the contrast echo method is to perform evaluation of hemodynamics by injecting a contrast agent from vein to enhance a blood flow signal in examination of the heart, liver, or the like. Many of contrast agents are designed so that microbubbles function as reflection sources. Recently, for example, a second generation ultrasound contrast agent called SONAZOID sold in Japan consists of microbubbles obtained by encapsulating perfluorobutane gas in phosphatide. The contrast echo method allows the state of reflux of the contrast agent to be observed in a stable manner by using a low or medium sound pressure ultrasonic wave for transmission which will not break the microbubbles.

By performing ultrasonic scanning on a diagnostic site (e.g., liver cancer) after injection of the contrast agent, an operator such as a doctor can observe an increase and a decrease of a signal intensity during a period from the inflow of the contrast agent being refluxed by blood flow to the outflow thereof. Moreover, a research for performing differential diagnosis of benign or malignant of mass lesion or diagnosis of any disease such as "diffuse" is also carried out from the difference in the change over time of the signal intensity.

The change over time of the signal intensity indicating reflux dynamics of the contrast agent is different from mere form information, and therefore there is a need to generally read a moving image in real time or after recording. Thus, the time require for reading the reflux dynamics of the contrast agent generally becomes long. Therefore, a technique for mapping the time information for the inflow of the contrast agent generally observed in a moving image on one still image has been proposed. The technique is configured to generate and display a still image representing a difference in peak time between signals of the contrast agent using different hues. By referring to the still image, a diagnostic reading person can easily grasp the inflow time at various places in a tomographic plane of the diagnostic site. In addition, a technique for generating and displaying a still image representing a difference in stagnant time (period of time from the start of inflow to the end of outflow) of the contrast agent in a specific area using different hues has been proposed.

Because running in a tumor blood vessel is complex as compared with a normal blood vessel, a phenomenon such that microbubbles nowhere to go stagnate in the tumor and further the stagnant microbubbles flow backward is observed. The behavior of the microbubbles in the tumor blood vessel is actually observed in tumor-bearing mice on which contrast ultrasonic imaging has been performed. In other words, if the behavior of the microbubbles can be evaluated through the contrast ultrasonic imaging capable of bioimaging, the contrast echo method is likely to be applicable also to evaluation of abnormality in tumor blood vessels.

Recently, it is confirmed by histopathological observation that an angiogenesis inhibitor, which is an anti-cancer agent that clinical trials are being carried out, destroys the blood vessel nourishing the tumor and causes fragmentation or narrowing of the tumor blood vessel. If it is possible to visualize or quantize, by the contrast ultrasonic imaging, how contrast ultrasonic observation is interrupted in the blood vessel fragmented by the angiogenesis inhibitor, the contrast echo method is expected to be applied to determination of therapeutic effect. However, in the conventional technology, there is a certain limit to the accuracy of quantitative analysis using the contrast echo method.

DETAILED DESCRIPTION

According to an embodiment, an ultrasonic diagnostic apparatus includes processing circuitry. The processing circuitry is configured to extract a first position through comparison of a fundamental wave component between a plurality pieces of image data collected by performing ultrasonic scanning on a subject injected with a contrast agent. The processing circuitry is configured to extract a second position through comparison of a harmonic component between the pieces of image data. The processing circuitry is configured to set either one of the first position and the second position as a position of a region of interest where predetermined analysis is performed in at least one image data of the pieces of image data.

Exemplary embodiments of an ultrasonic diagnostic apparatus will be explained in detail below with reference to the accompanying drawings.

First Embodiment

Figure 1:
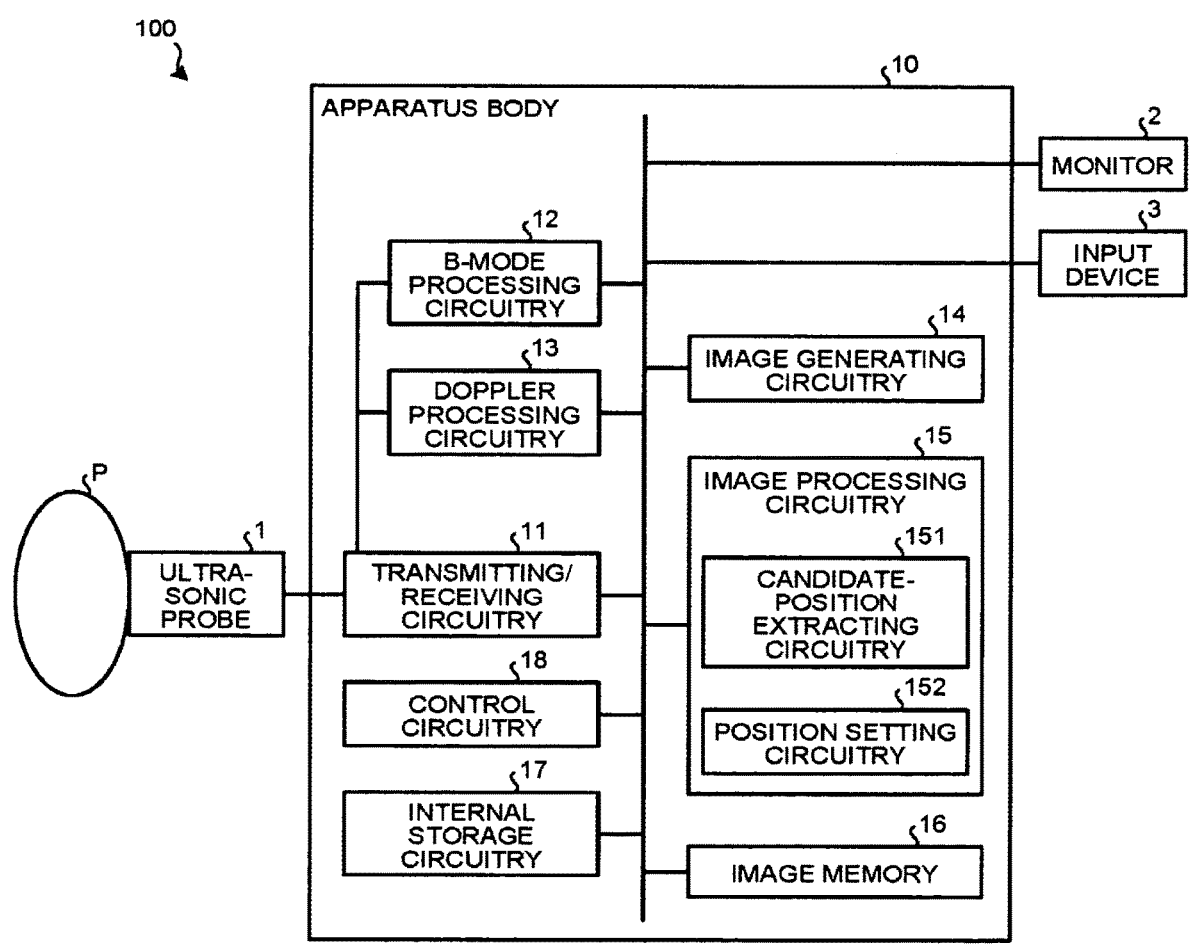
FIG. 1 is a block diagram of a configuration example of an ultrasonic diagnostic apparatus according to a first embodiment.

First of all, a configuration of an ultrasonic diagnostic apparatus according to a first embodiment will be explained below. FIG. 1 is a block diagram of a configuration example of an ultrasonic diagnostic apparatus 100 according to the first embodiment. As illustrated in FIG. 1, the ultrasonic diagnostic apparatus according to the first embodiment includes an ultrasonic probe 1, a monitor 2, an input device 3, and an apparatus body 10.

The ultrasonic probe 1 includes a plurality of piezoelectric transducer elements, and each of the piezoelectric transducer elements generates an ultrasonic wave based on a drive signal supplied from transmitting/receiving circuitry 11 provided in the apparatus body 10, which is explained later. The ultrasonic probe 1 receives a reflected wave from a subject P and converts the reflected wave into an electric signal. The ultrasonic probe 1 includes a matching layer provided in the piezoelectric transducer element, a backing material to prevent propagation of the ultrasonic wave from the piezoelectric transducer element to the rear side, and the like. The ultrasonic probe 1 is detachably connected to the apparatus body 10.

When an ultrasonic wave is transmitted from the ultrasonic probe 1 to the subject P, the transmitted ultrasonic wave is sequentially reflected by a discontinuous surface of acoustic impedance in the body tissue of the subject P, and the reflected ultrasonic waves are received as reflected wave signals by the piezoelectric transducer elements provided in the ultrasonic probe 1. The amplitude of the received reflected wave signal depends on a difference in acoustic impedance on the discontinuous surface that reflects the ultrasonic wave. When a transmitted ultrasonic pulse is reflected by a surface of a moving blood flow and a heart wall, the reflected wave signal is subjected to frequency shift depending on a velocity component of a moving body in an ultrasonic transmission direction by Doppler effect.

For example, the apparatus body 10, as an ultrasonic probe 1 for two-dimensional scanning, is connected to a in array probe in which a plurality of piezoelectric transducer elements are arrayed in a row. Alternatively, for example, the apparatus body 10, as an ultrasonic probe 1 for three-dimensional scanning, is connected to a mechanical 4D probe or to a 2D array probe. The mechanical 4D probe is capable of two-dimensional scanning by using a plurality of piezoelectric transducer elements arrayed in a row as the in array probe, and is capable of three-dimensional scanning by swinging the piezoelectric transducer elements at a predetermined angle (swing angle). The 2D array probe is capable of three-dimensional scanning by a plurality of piezoelectric transducer elements arranged in a matrix, and is capable of two-dimensional scanning by sending converged ultrasonic wave.

The present embodiment is applicable to a case where the subject P is two-dimensionally scanned by the ultrasonic probe 1 and even to a case where it is three-dimensionally scanned thereby.

The input device 3 includes a mouse, a keyboard, a button, a panel switch, a touch command screen, a foot switch, a trackball, a joystick, and the like, and accepts various setting requests from an operator of the ultrasonic diagnostic apparatus and forwards the accepted various setting requests to the apparatus body 10. For example, the input device 3 accepts various operations to perform quantitative analysis using the contrast echo method from the operator.

The monitor 2 displays a graphical user interface (GUI) used by the operator of the ultrasonic diagnostic apparatus inputting the various setting requests through the input device 3, or displays an ultrasonic image generated in the apparatus body 10 or a position of a site of interest in the ultrasonic image.

The apparatus body 10 is a device that generates ultrasonic image data based on the reflected wave signal received by the ultrasonic probe 1. The apparatus body 10 illustrated in FIG. 1 is a device capable of generating two-dimensional ultrasonic image data based on two-dimensional reflected wave data received by the ultrasonic probe 1. In addition, the apparatus body 10 illustrated in FIG. 1 is a device capable of generating three-dimensional ultrasonic image data based on three-dimensional reflected wave data received by the ultrasonic probe 1. Hereinafter, the three-dimensional ultrasonic image data may be described as "volume data".

As illustrated in FIG. 1, the apparatus body 10 includes the transmitting/receiving circuitry 11, B-mode processing circuitry 12, Doppler processing circuitry 13, image generating circuitry 14, image processing circuitry 15, image memory 16, internal storage circuitry 17, and control circuitry 18.

The transmitting/receiving circuitry 11 includes a pulse generator, transmission delay circuitry, a pulser, and the like, and supplies a drive signal to the ultrasonic probe 1. The pulse generator repeatedly generates rate pulses for formation of transmission ultrasonic waves at a predetermined rate frequency. The transmission delay circuitry provides a delay time for each piezoelectric transducer element required to converge ultrasonic waves generated from the ultrasonic probe 1 into a shape of beam and to determine transmission directivity to each rate pulse generated by the pulse generator. The pulser applies a drive signal (drive pulse) to the ultrasonic probe 1 at the timing based on the rate pulse. In other words, the transmission delay circuitry changes the delay time to be provided to each rate pulse and thereby arbitrarily adjusts the transmission direction of the ultrasonic wave transmitted from the surface of the piezoelectric transducer element.

The transmitting/receiving circuitry 11 has a function capable of instantly changing a transmission frequency, a transmission drive voltage, and the like in order to execute a predetermined scan sequence based on an instruction from the control circuitry 18, which will be explained later. In particular, the change in the transmission drive voltage is implemented by a linear amplifier transmission circuit capable of instantly switching the value or by a mechanism for electrically switching a plurality of power supply units.

The transmitting/receiving circuitry 11 also includes a preamplifier, an analog/digital (A/D) converter, reception delay circuitry, an adder, and the like, and performs various types of processing on the reflected wave signal received by the ultrasonic probe 1 to generate reflected wave data. The preamplifier amplifies the reflected wave signal for each channel. The A/D converter performs A/D conversion on the amplified reflected wave signal. The reception delay circuitry provides a delay time required to determine reception directivity. The adder performs addition processing on the reflected wave signal processed by the reception delay circuitry to generate reflected wave data. A reflection component reached from the direction according to the reception directivity of the reflected wave signal is enhanced through the addition processing performed by the adder, and comprehensive beam for ultrasonic transmission and reception is formed by the reception directivity and the transmission directivity.

When performing two-dimensional scanning on the subject P, the transmitting/receiving circuitry 11 transmits a two-dimensional ultrasonic beam from the ultrasonic probe 1. The transmitting/receiving circuitry 11 then generates two-dimensional reflected wave data from the two-dimensional reflected wave signal received by the ultrasonic probe 1. When performing three-dimensional scanning on the subject P, the transmitting/receiving circuitry 11 transmits a three-dimensional ultrasonic beam from the ultrasonic probe 1. The transmitting/receiving circuitry 11 then generates three-dimensional reflected wave data from the three-dimensional reflected wave signal received by the ultrasonic probe 1.

As for the form of an output signal from the transmitting/receiving circuitry 11, various forms, such as a signal including phase information called Radio Frequency (RF) signal or amplitude information after envelope detection processing, are selectable.

The B-mode processing circuitry 12 receives the reflected wave data from the transmitting/receiving circuitry 11, performs logarithmic amplification and envelope detection processing, etc., on the reflected wave data, and generates data (B-mode data) whose signal intensity is expressed by the brightness of luminance.

The B-mode processing circuitry 12 can change a frequency band to be imaged by changing a detection frequency. The contrast echo method, for example, contrast harmonic imaging (CHI) can be executed by using the function of the B-mode processing circuitry 12. That is, the B-mode processing circuitry 12 can separate the reflected wave data (harmonic data or subharmonic data) in which microbubbles function as reflection sources and the reflected wave data (fundamental wave data) in which tissue in the subject P functions as a reflection source, from the reflected wave data of the subject P injected with the ultrasound contrast agent. Thereby the B-mode processing circuitry 12 can extract the harmonic data or the subharmonic data from the reflected wave data of the subject P to generate B-mode data for generating contrast image data. The B-mode processing circuitry 12 can also extract the fundamental wave data from the reflected wave data of the subject P to generate B-mode data for generating tissue image data.

The Doppler processing circuitry 13 performs frequency analysis of velocity information from the reflected wave data received from the transmitting/receiving circuitry 11, extracts blood flow, tissue, and a contrast agent echo component due to the Doppler effect, and generates data (Doppler data) by extracting mobile body information on speed, dispersion, power, and the like for multiple points.

The B-mode processing circuitry 12 and the Doppler processing circuitry 13 according to the present embodiment can perform processing on both the two-dimensional reflected wave data and the three-dimensional reflected wave data. In other words, the B-mode processing circuitry 12 generates two-dimensional B-mode data from the two-dimensional reflected wave data, and generates three-dimensional B-mode data from the three-dimensional reflected wave data. The Doppler processing circuitry 13 generates two-dimensional Doppler data from the two-dimensional reflected wave data, and generates three-dimensional Doppler data from the three-dimensional reflected wave data.

The image generating circuitry 14 generates ultrasonic image data from the data generated by the B-mode processing circuitry 12 and the Doppler processing circuitry 13. That is, the image generating circuitry 14 generates two-dimensional B-mode image data, in which the intensity of the reflected wave is expressed by the luminance, from the two-dimensional B-mode data generated by the B-mode processing circuitry 12. The image generating circuitry 14 also generates two-dimensional Doppler image data representing the mobile body information from the two-dimensional Doppler data generated by the Doppler processing circuitry 13. The two-dimensional Doppler image data is a speed image, a dispersion image, a power image, or an image in combination with these images.

Generally, the image generating circuitry 14 converts a scan line signal string for ultrasonic scanning into a scan line signal string for a video format typified by television, etc. (scan conversion), and generates ultrasonic image data for display. Specifically, the image generating circuitry 14 generates ultrasonic image data for display by performing coordinate conversion according to ultrasonic scanning form by the ultrasonic probe 1. As various types of image processing other than the scan conversion, the image generating circuitry 14 uses, for example, a plurality of image frames after the scan conversion to perform image processing (smoothing processing) for re-generating an image with an average value of the luminance and to perform image processing (edge enhancement processing) using a differential filter within an image, and the like. The image generating circuitry 14 synthesizes character information of various parameters, scale marks, or a body mark in the ultrasonic image data.

In other words, the B-mode data and the Doppler data are the ultrasonic image data before the scan conversion processing, and the data generated by the image generating circuitry 14 is the ultrasonic image data for display after the scan conversion processing. The B-mode data and the Doppler data are also called Raw Data.

Moreover, the image generating circuitry 14 generates three-dimensional B-mode image data by performing coordinate conversion on the three-dimensional B-mode data generated by the B-mode processing circuitry 12. The image generating circuitry 14 generates three-dimensional Doppler image data by performing coordinate conversion on the three-dimensional Doppler data generated by the Doppler processing circuitry 13. That is, the image generating circuitry 14 generates "three-dimensional B-mode data or three-dimensional Doppler image data" as "three-dimensional ultrasonic image data (volume data)".

In addition, the image generating circuitry 14 performs rendering processing on the volume data in order to generate various pieces of two-dimensional image data for displaying the voltage data on the monitor 2. The rendering processing performed by the image generating circuitry 14 includes processing for performing Multi Planer Reconstruction (MPR) to generate MPR image data from the voltage data. The rendering processing performed by the image generating circuitry 14 also includes processing for performing "Curved MPR" on the voltage data and processing for performing "Maximum Intensity Projection" on the voltage data. The rendering processing performed by the image generating circuitry 14 further includes Volume Rendering (VR) processing for generating two-dimensional image data that reflects three-dimensional information.

The image memory 16 is a memory that stores the image data for display generated by the image generating circuitry 14. The image memory 16 can store data generated by the B-mode processing circuitry 12 and the Doppler processing circuitry 13. The image data for display stored in the image memory 16 can be called by the operator, for example, after diagnosis. The B-mode data and the Doppler data stored in the image memory 16 can also be called by the operator, for example, after diagnosis, and these data are provided as ultrasonic image data for display via the image generating circuitry 14. The image memory 16 can also store the data output from the transmitting/receiving circuitry 11.

The image processing circuitry 15 is provided in the apparatus body 10 to perform Computer-Aided Diagnosis (CAD). The image processing circuitry 15 acquires data stored in the image memory 16 and performs image processing thereon. The image processing circuitry 15 then stores the result of image processing in the image memory 16 or in the internal storage circuitry 17, which will be explained later. The processing performed by the image processing circuitry 15 will be explained later.

The internal storage circuitry 17 stores control programs for performing ultrasonic transmission and reception, image processing, and display processing; diagnostic information (e.g., patient ID, doctor's findings); diagnostic protocol; and various pieces of data such as various body marks. The internal storage circuitry 17 is also used for storage of the image data stored by the image memory 16 if necessary. The data stored in the internal storage circuitry 17 can be forwarded to an external device via an interface (not illustrated). Examples of the external device include, but are not limited to, various medical diagnostic imaging apparatuses, a personal computer (PC) used by a doctor performing diagnostic imaging, a storage medium such as CD and DVD, and a printer.

The control circuitry 18 controls the entire processing of the ultrasonic diagnostic apparatus. Specifically, the control circuitry 18 controls respective processings of the transmitting/receiving circuitry 11, the B-mode processing circuitry 12, the Doppler processing circuitry 13, the image generating circuitry 14, and the image processing circuitry 15, based on various setting requests input by the operator through the input device 3 and various control programs and various data read from the internal storage circuitry 17. The control circuitry 18 provides control so as to display the image data stored in the image memory 16 or in the internal storage circuitry 17 on the monitor 2.

As explained above, the overall configuration of the ultrasonic diagnostic apparatus according to the present embodiment has been explained. Under such a configuration, the ultrasonic diagnostic apparatus according to the first embodiment makes it possible to improve the accuracy of quantitative analysis using the contrast echo method by the processing of the image processing circuitry 15, which will be explained in detail below. A case where the accuracy is degraded in the quantitative analysis of the conventional contrast echo method will be explained herein. For example, as a method of quantitative analysis by the contrast echo method, analysis using Time Curve Analysis (TCA) is known. For example, by analyzing time change of the contrast agent within an analysis area such as a region of interest, the TCA can check the feature of tumor or check the change over time of treatment.

In the TCA, it is required to always capture the region of interest as an analysis area in order to maintain the quantitative accuracy. However, there is a case where the position of the region of interest in the ultrasonic scanning area fluctuates depending on patient's breathing, beating of the heart, or movement of the operator. Therefore, as a technology responding to the fluctuation of the region of interest, a technology of dynamically tracking the region of interest using the data for a harmonic image is known. However, because the data for the harmonic image has an intense change before and after contrast, there is a certain limit to the tracking accuracy of the region of interest. In addition, because the harmonic image before reaching of the contrast agent is almost black, it is difficult to specify the region of interest.

In this way, in the conventional technology, because there is a certain limit to the accuracy of tracking the fluctuation of the region of interest, there is also a certain limit to the accuracy of the quantitative analysis on the region of interest as a target. Therefore, in the ultrasonic diagnostic apparatus 100 according to the first embodiment, the region of interest can be accurately detected by the processing performed by the image processing circuitry 15, which makes it possible to improve the accuracy of the quantitative analysis using the contrast echo method.

As illustrated in FIG. 1, the image processing circuitry 15 includes candidate-position extracting circuitry 151 and position setting circuitry 152. The candidate-position extracting circuitry 151 extracts a first position through comparison of a fundamental wave component between a plurality pieces of image data collected by performing ultrasonic scanning on a subject injected with the contrast agent. The candidate-position extracting circuitry 151 also extracts a second position through comparison of a harmonic component between the pieces of image data. Specifically, the candidate-position extracting circuitry 151 extracts first positions of the region of interest included in respective time-series image data collected by performing ultrasonic scanning performed on a subject injected with the contrast agent, based on the similarity of the fundamental wave components between the time-series image data. The candidate-position extracting circuitry 151 also extracts second positions of the region of interest included in respective time-series image data based on the similarity of the harmonic components between the time-series image data.

For example, the candidate-position extracting circuitry 151 compares a fundamental wave component in a region set in a predetermined position in predetermined image data included in a plurality pieces of image data and fundamental wave components in a plurality of regions set in a plurality of positions corresponding to a predetermined position in another image data different from the predetermined image data included in the pieces of image data, and extracts the position, as the first position, corresponding to the region, of the regions, having the fundamental wave component most similar to the fundamental wave component in the region set in the predetermined position in the predetermined image data. The candidate-position extracting circuitry 151 compares a harmonic component in a region set in a predetermined position in predetermined image data and harmonic components in a plurality of regions set in a plurality of positions corresponding to predetermined positions in another image data, and extracts the position, as the second position, corresponding to the region, of the regions, having the harmonic component most similar to the harmonic component in the region set in the predetermined position in the predetermined image data.

Figure 2A:
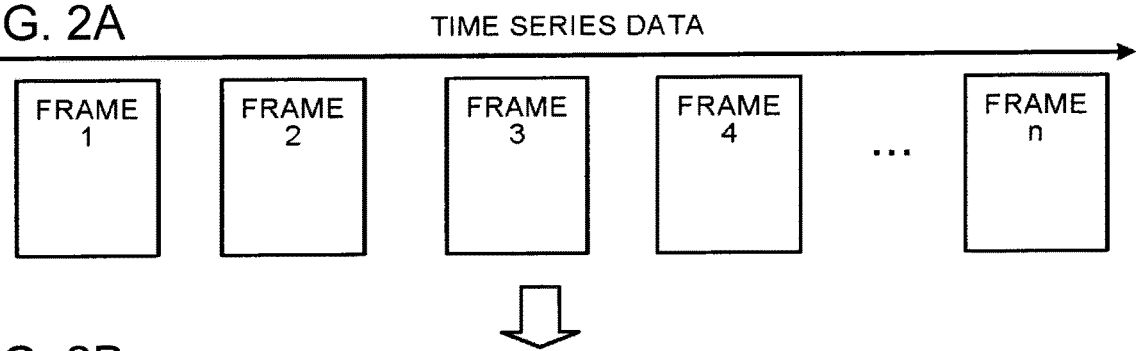
FIGS. 2A-C are diagrams for explaining an example of a target to be processed by candidate-position extracting circuitry according to the first embodiment.
Figure 2B:
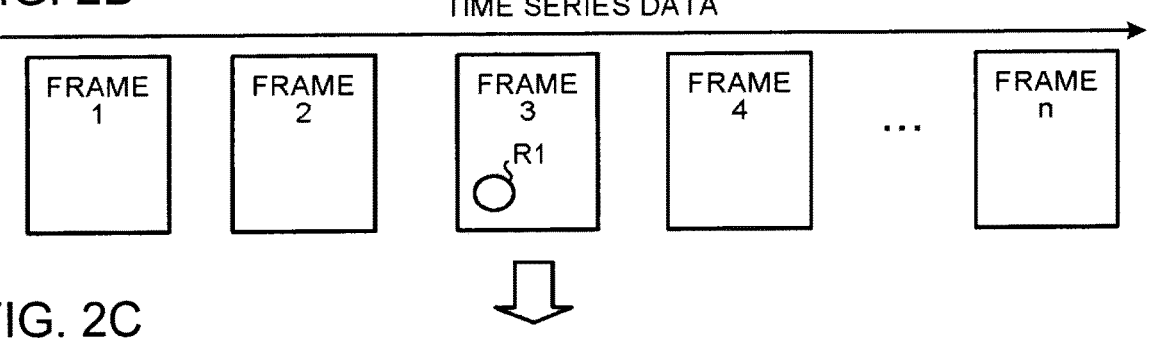
Figure 2C:
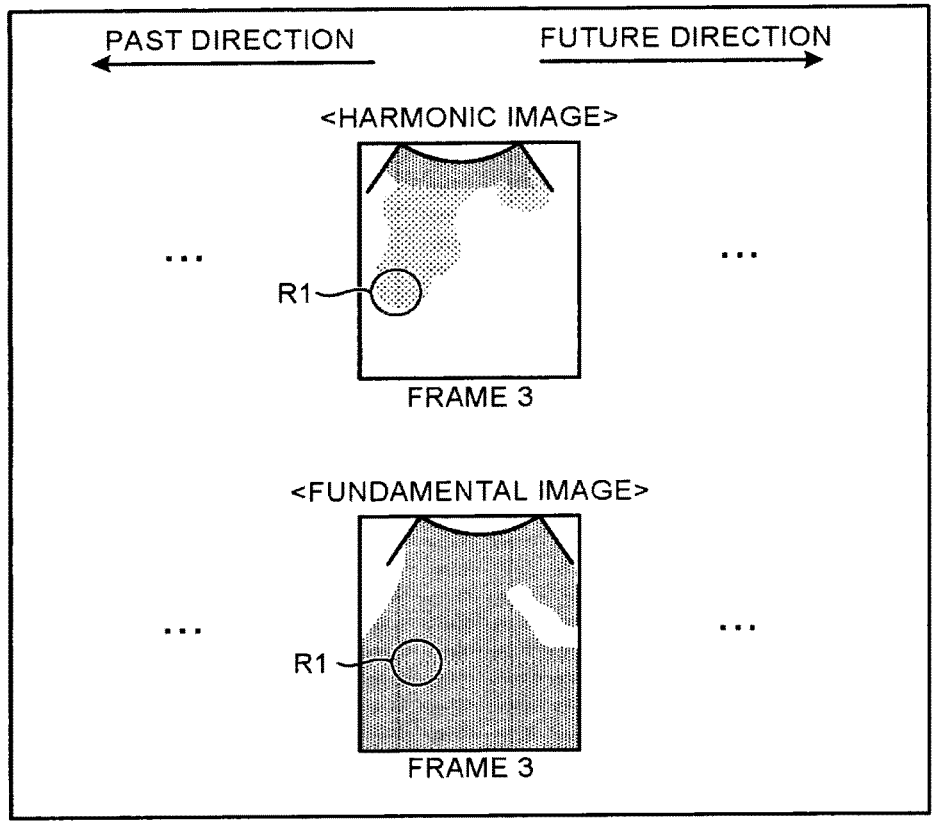

FIGS. 2A-C are diagrams for explaining an example of a target to be processed by the candidate-position extracting circuitry 151 according to the first embodiment. For example, as illustrated in FIG. 2A, the candidate-position extracting circuitry 151 performs detection processing for the region of interest on time series data from frame 1 to frame n collected by performing ultrasonic scanning on the patient injected with the contrast agent. In FIGS. 2A-C, the time series frames are arranged in the order from the frame 1.

For example, as illustrated in FIG. 2B, when a region of interest R1 is set in the frame 3, the candidate-position extracting circuitry 151 extracts a harmonic image formed from the harmonic component of the image data for the frame 3 and a fundamental image formed from the fundamental wave component, as illustrated in FIG. 2C. The region of interest set in the frame 3 may be set by the operator observing the time series data through the input device 3 or may be set by being automatically extracted through the processing such as pattern matching performed on each image data included in the time series data.

The candidate-position extracting circuitry 151 then extracts the harmonic image and the fundamental image from the frames of the time series data respectively, and extracts the position of the region of interest R1 in each of the images. Here, the candidate-position extracting circuitry 151 calculates similarities between a fundamental wave component in the region of interest set in the predetermined image data included in the time-series image data and fundamental wave components in a plurality of candidate regions, each of which has the same size as that of the region of interest, set in an area covering a region at the same position as that of the region of interest set in the time-series image data, and extracts the position of the candidate region with the highest similarity among the calculated ones as the first position.

Figure 3A:
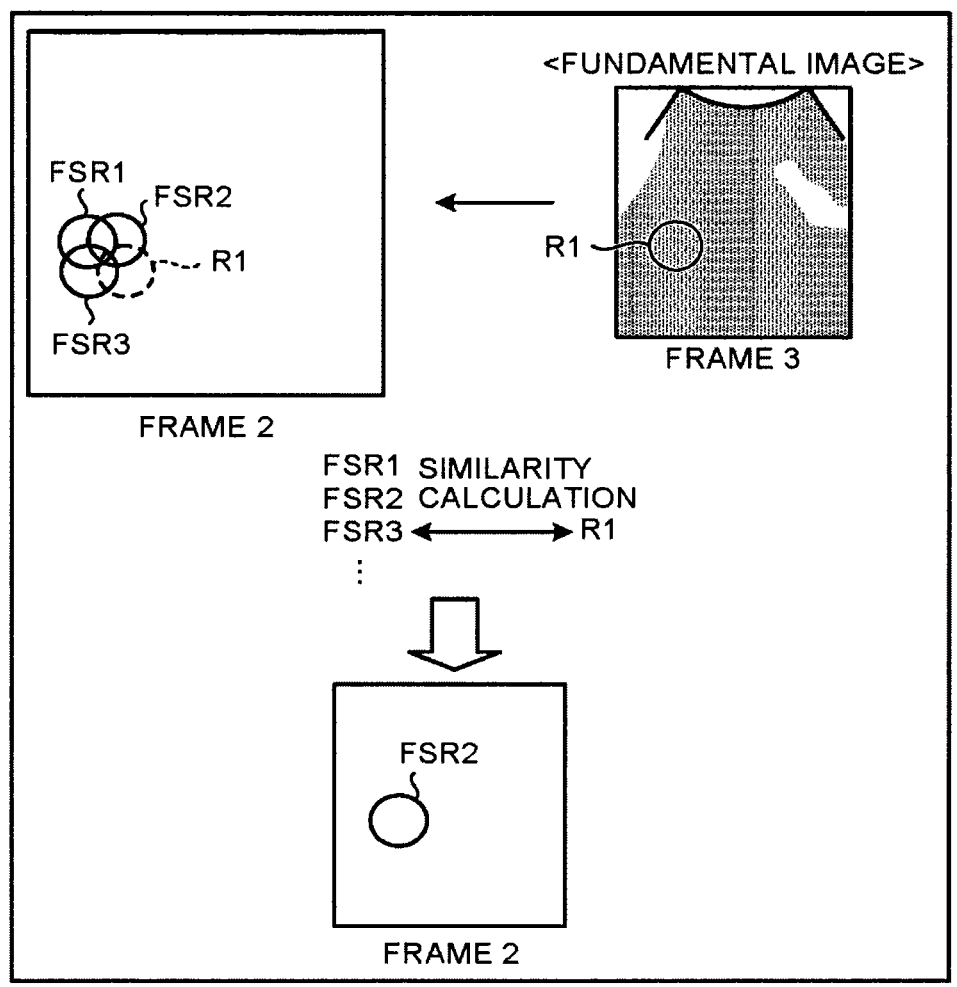
FIG. 3A is a diagram for explaining an example of how the candidate-position extracting circuitry according to the first embodiment extracts a region of interest in a fundamental image.

FIG. 3A is a diagram for explaining an example of how the candidate-position extracting circuitry 151 according to the first embodiment extracts the region of interest in the fundamental image. FIG. 3A represents a case of extracting candidate positions of the region of interest R1 in the fundamental image of the frame 2 based on the region of interest R1 set in the fundamental image of the frame 3. In FIG. 3A, although the frame 2 is represented larger than the frame 3 for the sake of description, both sizes are in fact the same. For example, when the region of interest R1 is set in the frame 3 as illustrated in FIG. 3A, the candidate-position extracting circuitry 151 acquires information on the center position (coordinates) of the region of interest R1 and the size of the region (e.g., diameter).

In the fundamental image of the frame 2, when the region of interest R1 is set in the same position as the position of the region of interest R1 in the fundamental image of the frame 3, the candidate-position extracting circuitry 151 sets a plurality of sub-regions each with the same size as the region of interest R1 in an area covering the set region. For example, the candidate-position extracting circuitry 151 sets sub-regions FSR1, FSR2, FSR3, etc. that include pixels included in the region of interest R1. Although only FSR1 to FSR3 are represented in FIG. 3A, a large number of sub-regions are further set in an actual case. For example, the sub-regions FSR are set while shifting the pixels included in the region of interest R1 one by one.

The size of the area covering the region of interest R1 can be arbitrarily set. For example, it may be a case where the size of the area is determined by previously acquiring a change in the position of a target site in each time phase of breathing and estimating how the region of interest R1 changes from the time phase of the breathing in the frame where the position of the region of interest R1 is set. In the example, the breathing is cited as an example; however, there may be a case of using a cardiac phase or there may be a case where the hardness or the like of a test site is considered.

The candidate-position extracting circuitry 151 calculates respective similarities between the set sub-regions and the region of interest R1 in the frame 3. For example, as illustrated in FIG. 3A, the candidate-position extracting circuitry 151 sequentially calculates the similarity between the region of interest R1 and the sub-region FSR1, the similarity between the region of interest R1 and the sub-region FSR2, and the similarity between the region of interest R1 and the sub-region FSR3, and the like. For example, the similarity between the regions may be a case of using an average value of pixel values, or may be a case of using a histogram of pixel values. In other words, it may be a case of using any method if the method is capable of calculating the similarity between the images.

When the similarities between the regions are calculated, the candidate-position extracting circuitry 151 extracts a sub-region FSR indicating the highest similarity among the calculated similarities as a candidate position of the region of interest R1 in the fundamental image. For example, as illustrated in FIG. 3A, the candidate-position extracting circuitry 151 extracts the sub-region FSR2 as the candidate position of the region of interest R1 in the fundamental image.

Moreover, the candidate-position extracting circuitry 151 calculates similarities between a harmonic component in the region of interest set in predetermined image data and harmonic components in a plurality of candidate regions, each of which has the same size as that of the region of interest, set in an area covering a region at the same position as that of the region of interest set in the time-series image data, and extracts the position of the candidate region with the highest similarity among the calculated ones as the second position.

Figure 3B:
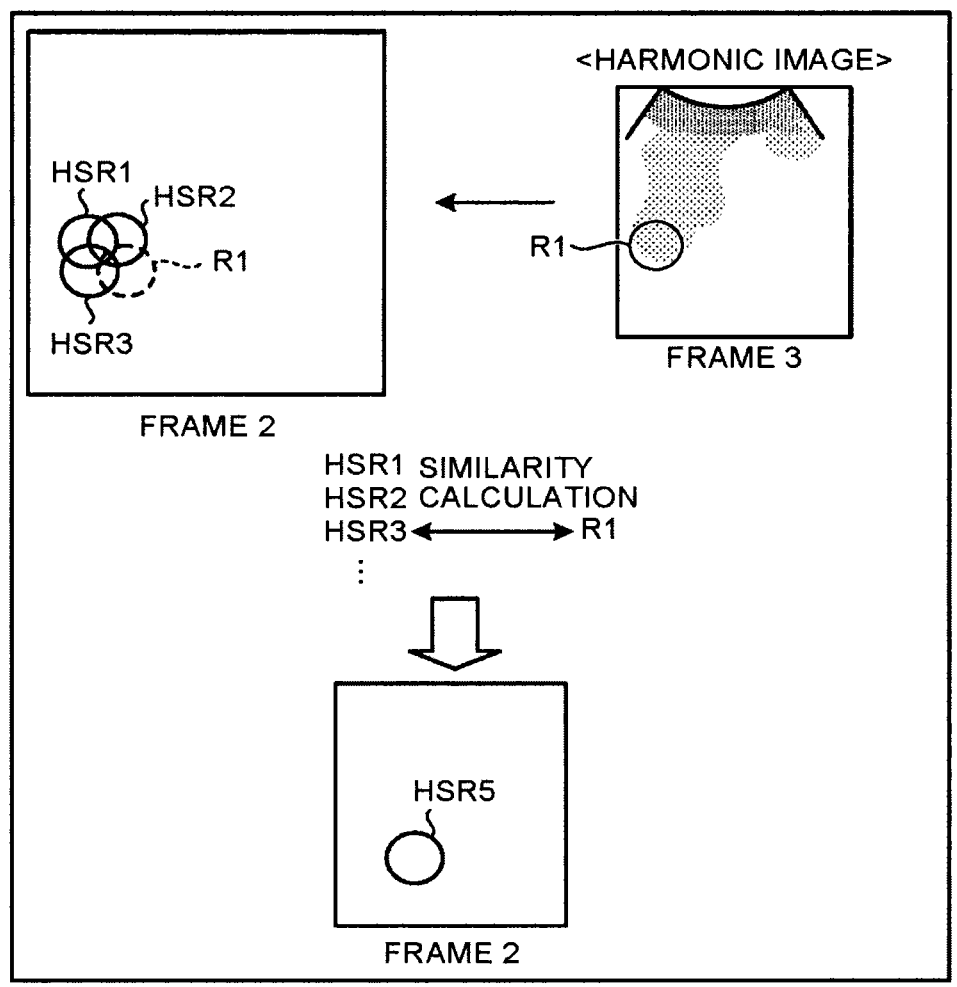
FIG. 3B is a diagram for explaining an example of how the candidate-position extracting circuitry according to the first embodiment extracts a region of interest in a harmonic image.

FIG. 3B is a diagram for explaining an example of how the candidate-position extracting circuitry according to the first embodiment extracts the region of interest in the harmonic image. FIG. 3B represents a case of extracting candidate positions of the region of interest R1 in the harmonic image of the frame 2 based on the region of interest R1 set in the harmonic image of the frame 3. In FIG. 3B, although the frame 2 is represented larger than the frame 3 for the sake of description, both sizes are in fact the same. For example, when the region of interest R1 is set in the frame 3 as illustrated in FIG. 3B, the candidate-position extracting circuitry 151 acquires information on the center position (coordinates) of the region of interest R1 and the size of the region (e.g., diameter).

In the harmonic image of the frame 2, when the region of interest R1 is set in the same position as the position of the region of interest R1 in the harmonic image of the frame 3, the candidate-position extracting circuitry 151 sets a plurality of sub-regions each with the same size as the region of interest R1 in an area covering the set region. For example, the candidate-position extracting circuitry 151 sets sub-regions HSR1, HSR2, HSR3, etc. that include pixels included in the region of interest R1. Although only HSR1 to HSR3 are represented in FIG. 3B, a large number of sub-regions are further set in an actual case. For example, the sub-regions HSR are set while shifting the pixels included in the region of interest R1 one by one. The size of the area covering the region of interest R1 can be arbitrarily set similarly to the above case.

The candidate-position extracting circuitry 151 calculates respective similarities between the set sub-regions and the region of interest R1 in the frame 3. For example, as illustrated in FIG. 3B, the candidate-position extracting circuitry 151 sequentially calculates the similarity between the region of interest R1 and the sub-region HSR1, the similarity between the region of interest R1 and the sub-region HSR2, and the similarity between the region of interest R1 and the sub-region HSR3, and the like. The similarity between the regions may be a case of using an average value of pixel values, or may be a case of using a histogram of pixel values. In other words, it may be a case of using any method if the method is capable of calculating the similarity between the images.

When the similarities between the regions are calculated, the candidate-position extracting circuitry 151 extracts a sub-region HSR indicating the highest similarity among the calculated similarities as a candidate position of the region of interest R1 in the harmonic image. For example, as illustrated in FIG. 3B, the candidate-position extracting circuitry 151 extracts a sub-region HSR5 as the candidate position of the region of interest R1 in the harmonic image. A variety of similarity calculation methods can be applied to the similarity calculation in the fundamental image and to the similarity calculation in the harmonic image; however, one and the same method is applied to both of the cases.

Referring back to FIG. 1, the position setting circuitry 152 sets either one of the first position and the second position in each of the time-series image data as the position of the region of interest based on the feature of a pixel in the region at the first position and the feature of a pixel in the region at the second position. Specifically, the position setting circuitry 152 sets the position with a higher similarity, as the position of the region of interest, between the similarity of the fundamental wave component at the first position and the similarity of the harmonic component at the second position.

Figures 4A, 4B:
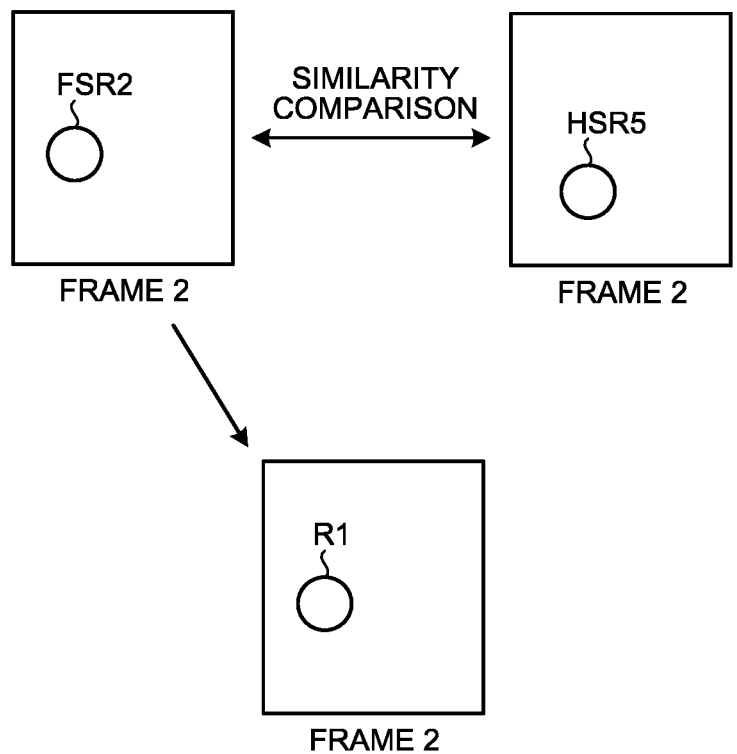
FIG. 4A is a diagram for explaining an example of processing performed by position setting circuitry according to the first embodiment.
FIG. 4B is a diagram of an example of information for regions of interest stored by the position setting circuitry according to the first embodiment.

FIG. 4A is a diagram for explaining an example of processing performed by the position setting circuitry 152 according to the first embodiment. For example, as illustrated in FIG. 4A, the position setting circuitry 152 compares the similarity of the sub-region FSR2 being the candidate position of the region of interest R1 extracted from the fundamental image by the candidate-position extracting circuitry 151 and the similarity of the sub-region HSR5 being the candidate position of the region of interest R1 extracted from the harmonic image, and sets the position of the sub-region FSR2 with a higher similarity as the position of the region of interest R1 in the frame 2.

The position setting circuitry 152 sets the first position or the second position as a position of the region of interest on condition that a variance value of the pixel value in the region at the first position or at the second position exceeds a predetermined threshold. For example, when the position of the region of interest R1 in the frame 2 is to be set as the position of the sub-region FSR2 of the fundamental image, the position setting circuitry 152 calculates the variance value of the pixel value included in the sub-region FSR2, and compares the calculated variance value and the predetermined threshold. When the variance value of the pixel value included in the sub-region FSR2 exceeds the predetermined threshold as a result of comparison, the position setting circuitry 152 sets the position of the sub-region FSR2 as the position of the region of interest R1 in the frame 2. This makes it possible to determine the region where the site of interest is clearly visualized as the region of interest.

When the region of interest is set, the position setting circuitry 152 stores the information for the set region of interest in, for example, the internal storage circuitry 17. FIG. 4B is a diagram of an example of information for regions of interest stored by the position setting circuitry 152 according to the first embodiment. As illustrated in FIG. 4B, the position setting circuitry 152 stores information for the region of interest associated with Center of Region of Interest, Size of Region of Interest, and Flag for each frame in the internal storage circuitry 17. The center of region of interest means coordinates of the center position of the set region of interest. The size of region of interest means the size of the region of interest. The flag means a flag indicating whether to use the information for the region of interest of the corresponding frame.

For example, when the region of interest R1 is set in the frame 3, the position setting circuitry 152 stores the information for the set region of interest R1 "Frame: 3, Center of Region of Interest: (5, 5), Size of Region of Interest: 2 cm, Flag:—". Thereafter, the candidate-position extracting circuitry 151 acquires the information for the region of interest of the frame 3 illustrated in FIG. 4B and performs the processing, and the position setting circuitry 152 stores "Center of Region of Interest: (6, 7)=(5, 5)+(1, 2), Size of Region of Interest: 2 cm, Flag:—" as the information for the region of interest of the frame 2.

Here, as illustrated in FIG. 4B, the position setting circuitry 152 can also store the information for "Center of Region of Interest" as the coordinate information "(6, 7)" after movement, or can also store the information for the coordinates "(5, 5)" of the region of interest R1 initially set and the information for offset "+(1, 2)". That is, the position setting circuitry 152 can also store the information indicating in which portion of each frame the region of interest is present, or can store the information indicating how far each frame moves from an initially set position based on the initially set region of interest.

Then, the processing is performed on all the frames of the time series data. In other words, the candidate-position extracting circuitry 151 extracts respective first positions in the normal order and the reverse order of the time series, based on the image data where the region of interest is set. Moreover, the candidate-position extracting circuitry 151 extracts respective second positions in the normal order and the reverse order of the time series, based on the image data where the region of interest is set. For example, when the region of interest R1 is set in the frame 3, the candidate-position extracting circuitry 151 extracts candidate positions indicating candidates of the position of the region of interest R1 in frame 4 from the fundamental image and the harmonic image respectively, similarly to the processing of the frame 2.

Figure 5:
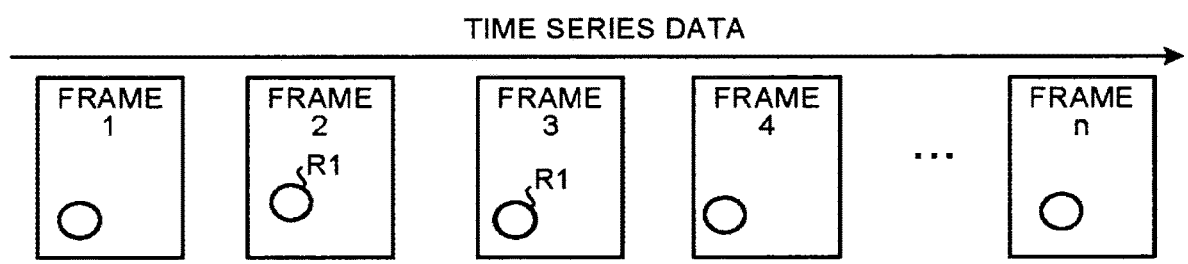
FIG. 5 is a diagram of an example of the regions of interest set by the ultrasonic diagnostic apparatus according to the first embodiment.

When the position setting circuitry 152 sets the position of the region of interest R1 in the frame 2 and stores the information for the region of interest R1, the candidate-position extracting circuitry 151 reads the information for the region of interest R1 of the frame 2 and extracts the candidate positions indicating the candidates of the position of the region of interest R1 in the frame 1 from the fundamental image and the harmonic image respectively. In this way, the candidate-position extracting circuitry 151 according to the first embodiment extracts positions of the region of interest from the fundamental image and the harmonic image for each frame of the time series data, compares the positions, and performs position setting of the region of interest with higher accuracy. Thereby the position of the region of interest R1 is set in all the frames of the time series data as illustrated in, for example, FIG. 5. FIG. 5 is a diagram of an example of the regions of interest set by the ultrasonic diagnostic apparatus 100 according to the first embodiment.

The positions of the region of interest illustrated in FIG. 5 are set by using both the fundamental image and the harmonic image, and therefore these positions are more accurate. As a result, by performing TCA using the regions of interest set in the frames illustrated in FIG. 5, the accuracy of quantitative analysis using the contrast echo method can be improved.

For the position setting of the region of interest, it is possible to set the positions of the region of interest in all the frames based on the frame in which the region of interest is set, or it is possible to set the positions of the region of interest between two frames which are continuous in time series. For example, it may be a case where the positions of the regions of interest are set in all the frames based on the position of the region of interest in the frame 3 where the position of the region of interest is initially set, or it may be a case where the position of the region of interest is set in the frame 2 based on the position of the region of interest in the frame 3 and the position of the region of interest is set in the frame 1 based on the position of the region of interest set in the frame 2. To understand, for example, a case of an error in operation of the ultrasonic probe or a case where a subject moves significantly, it is desirable to set the positions of the region of interest between two frames which are continuous in time series. In other words, when the similarity is lower than the predetermined threshold between the continuous frames, it is possible to assume the case of the error in operation of the ultrasonic probe or the case where the subject moves significantly.

Figure 6:
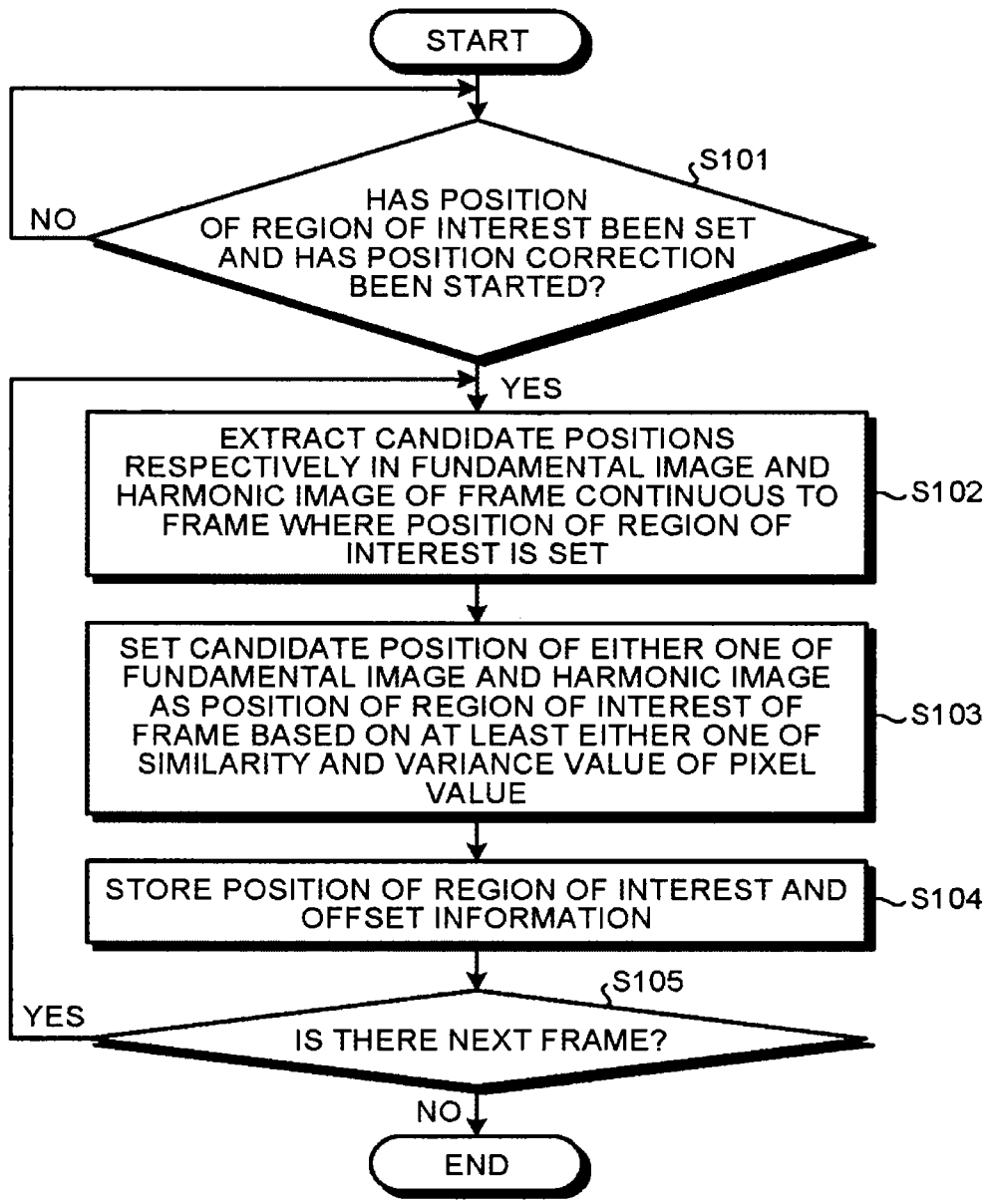
FIG. 6 is a flowchart (1) indicating a processing procedure performed by the ultrasonic diagnostic apparatus according to the first embodiment.

The processing of the ultrasonic diagnostic apparatus 100 according to the first embodiment will be explained next. FIG. 6 is a flowchart (1) indicating a processing procedure performed by the ultrasonic diagnostic apparatus 100 according to the first embodiment. In the ultrasonic diagnostic apparatus 100 according to the first embodiment, for example, as illustrated in FIG. 6, when the position of the region of interest is set and position correction is started (Yes at Step S101), the candidate-position extracting circuitry 151 extracts candidate positions respectively in the fundamental image and the harmonic image of a frame continuous to the frame where the position of interest is set (Step S102).

The position setting circuitry 152 sets the candidate position of either one of the fundamental image and the harmonic image as a position of the region of interest of the frame based on at least either one of the similarity and the variance value of the pixel value (Step S103), and stores the position of the set region of interest and the offset information (Step S104). The candidate-position extracting circuitry 151 then determines whether there is a next frame (Step S105).

When it is determined that there is a next frame (Yes at Step S105), the candidate-position extracting circuitry 151 returns to Step S102 and continues the processing. Meanwhile, when it is determined that there is no next frame (No at Step S105), the candidate-position extracting circuitry 151 ends the processing.

Figure 7:
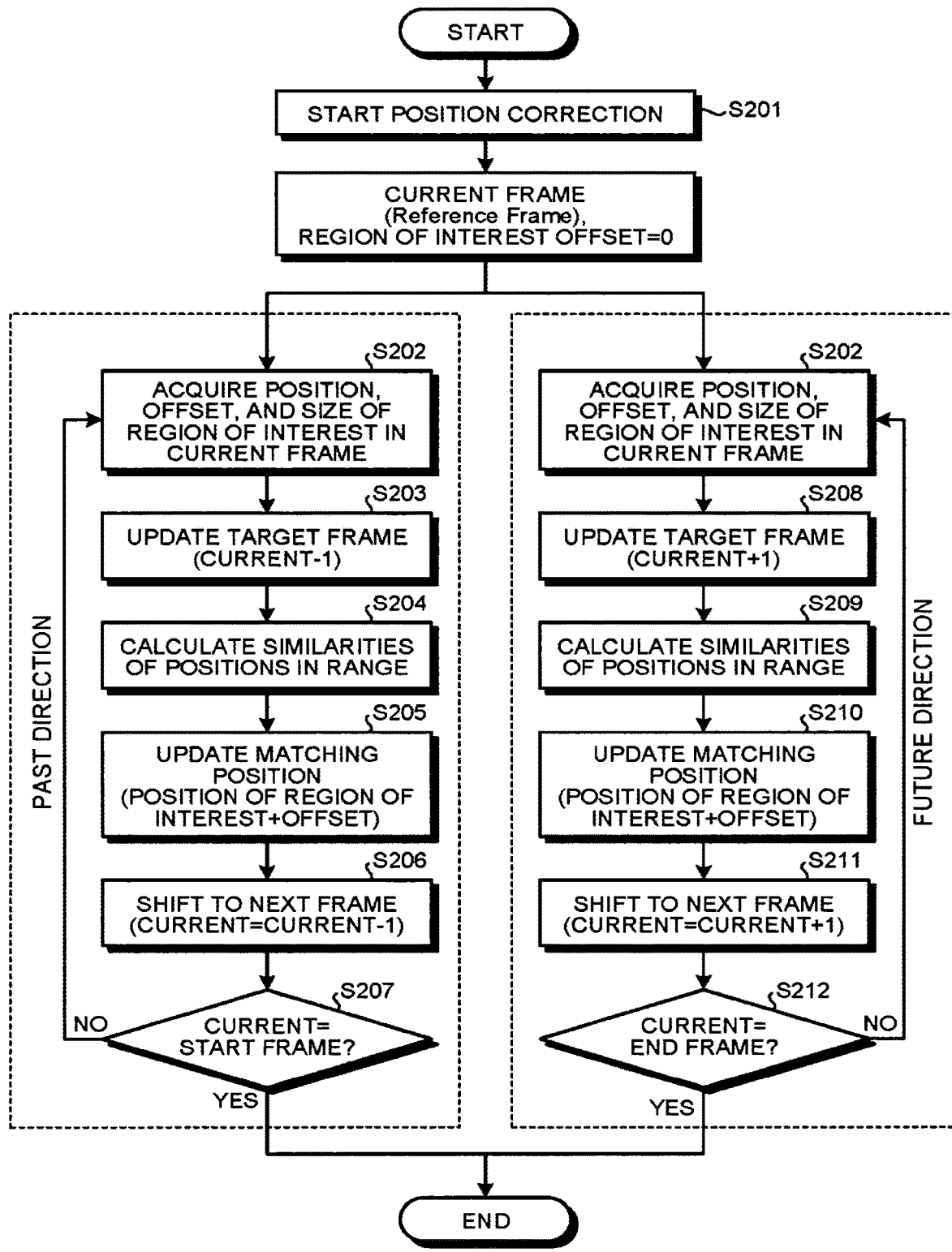
FIG. 7 is a flowchart (2) indicating the processing procedure performed by the ultrasonic diagnostic apparatus according to the first embodiment.

As explained above, the ultrasonic diagnostic apparatus 100 according to the first embodiment extracts the candidate positions for the regions of interest from the fundamental image and the harmonic image of each frame, and sets the position based on the similarity and the like. Details of the processing will be explained below with reference to FIG. 7. FIG. 7 is a flowchart (2) indicating the processing procedure performed by the ultrasonic diagnostic apparatus according to the first embodiment.

FIG. 7 represents a case where comparison between the candidate position of the fundamental image and the candidate position of the harmonic image is performed based on the similarity. As illustrated in FIG. 7, in the ultrasonic diagnostic apparatus 100 according to the first embodiment, when the position correction is started (Step S201), the candidate-position extracting circuitry 151 acquires a current frame (Reference Frame) and information for the region of interest offset=0. The ultrasonic diagnostic apparatus 100 according to the first embodiment performs the processing in the normal order and the reverse order in time series from the frame where the region of interest is set in the time series data. In FIG. 7, although smaller step numbers are assigned to a past direction, the processing in the past direction (reverse order) and the processing in a future direction (normal order) are in fact simultaneously performed.

Hereinafter, the processing in the past direction will be explained first. The candidate-position extracting circuitry 151 acquires the position, offset, and size of the region of interest in the current frame at Step S202. The candidate-position extracting circuitry 151 then updates the frame of a target frame (Current−1) (Step S203), and calculates respective similarities of positions in a predetermined range including the region of interest for the fundamental image and the harmonic image (Step S204). The position setting circuitry 152 sets the position corresponding to the highest similarity among the calculated similarities as a matching position of the region of interest, and updates the matching position (Position of region of interest+Offset) (Step S205).

Then, the candidate-position extracting circuitry 151 changes the position to (Current=Current−1) and shifts the target to the next frame (Step S206). The candidate-position extracting circuitry 151 determines whether the current frame is a start frame (Step S207). When it is determined that the current frame is the start frame (Yes at Step S207), the candidate-position extracting circuitry 151 ends the processing in the past direction. Meanwhile, when it is determined that the current frame is not the start frame (No at Step S207), the candidate-position extracting circuitry 151 returns to Step S202, and performs the processing on the next frame.

The processing in the future direction will be explained next. For the future direction, also, the candidate-position extracting circuitry 151 acquires the position, offset, and size of the region of interest in the current frame at Step S202. The candidate-position extracting circuitry 151 then updates the frame of a target frame (Current+1) (Step S208), and calculates respective similarities of positions in a predetermined range including the region of interest for the fundamental image and the harmonic image (Step S209). The position setting circuitry 152 sets the position corresponding to the highest similarity among the calculated similarities as a matching position of the region of interest, and updates the matching position (Position of region of interest+Offset) (Step S210).

Then, the candidate-position extracting circuitry 151 changes the position to (Current=Current+1) and shifts the target to the next frame (Step S211). The candidate-position extracting circuitry 151 determines whether the current frame is an end frame (Step S212). When it is determined that the current frame is the end frame (Yes at Step S212), the candidate-position extracting circuitry 151 ends the processing in the future direction. Meanwhile, when it is determined that the current frame is not the end frame (No at Step S212), the candidate-position extracting circuitry 151 returns to Step S202, and performs the processing on the next frame.

Figure 8:
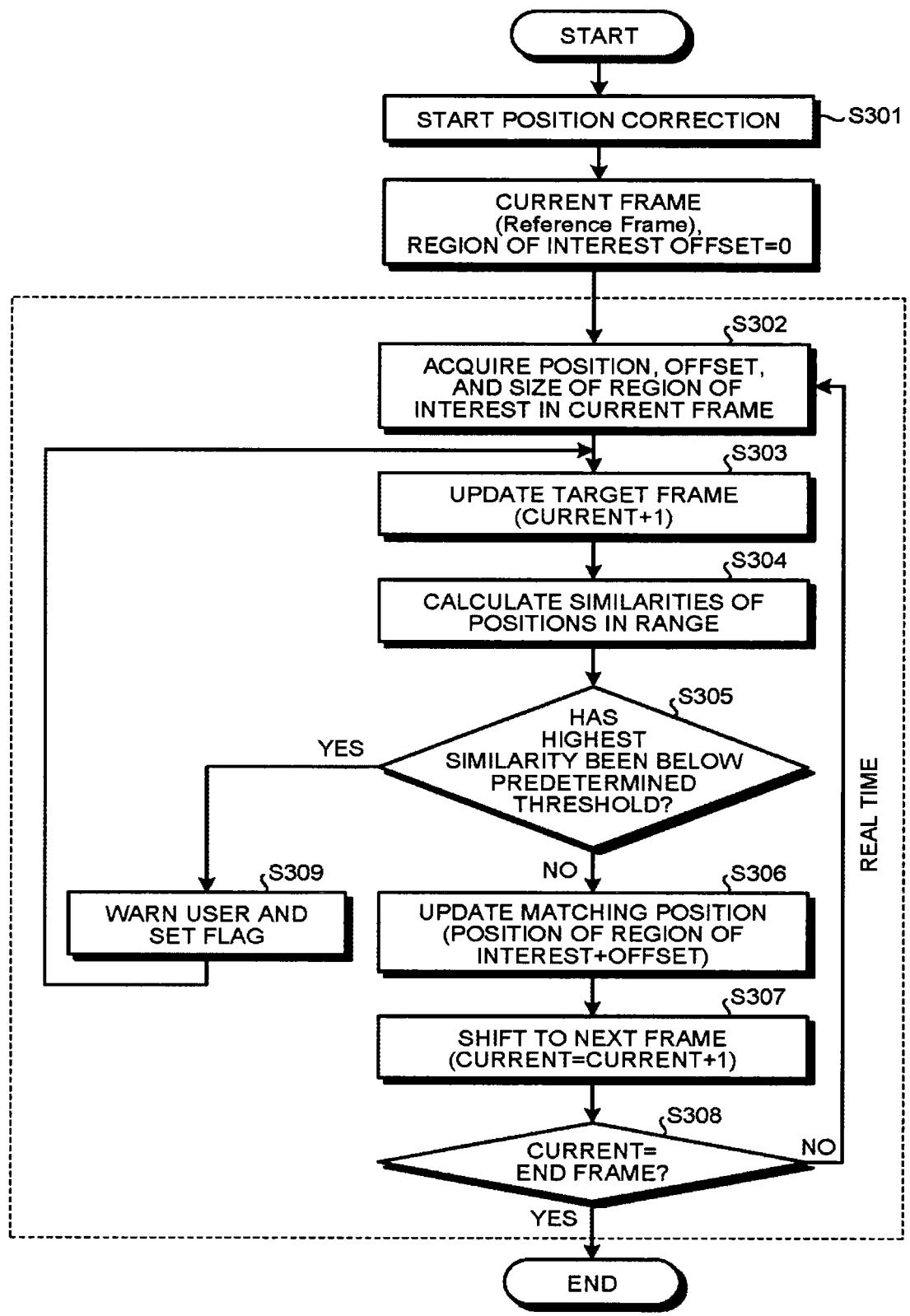
FIG. 8 is a flowchart (3) indicating the processing procedure performed by the ultrasonic diagnostic apparatus according to the first embodiment.

For the processing explained so far, the case of using the collected time series data has been explained. The ultrasonic diagnostic apparatus 100 according to the first embodiment can also be applied to a case where the time series data is collected in real time. FIG. 8 is a flowchart (3) indicating the processing procedure performed by the ultrasonic diagnostic apparatus 100 according to the first embodiment.

As illustrated in FIG. 8, in the ultrasonic diagnostic apparatus 100 according to the first embodiment, when the position correction is started (Step S301), the candidate-position extracting circuitry 151 acquires the current frame (Reference frame) and information for the region of interest offset=0. In other words, the candidate-position extracting circuitry 151 acquires the position, offset, and size of the region of interest in the current frame at Step S302 (Step S302). The candidate-position extracting circuitry 151 then updates the frame of the target frame (Current+1) (Step S303), and calculates respective similarities of positions in a predetermined range including the region of interest for the fundamental image and the harmonic image (Step S304). The position setting circuitry 152 determines whether the highest similarity among the calculated similarities is below the predetermined threshold (Step S305).

When it is determined that the highest similarity is not below the predetermined threshold (No at Step S305), the position setting circuitry 152 sets the position corresponding to the highest similarity as a matching position of the region of interest, and updates the matching position (Position of region of interest+Offset) (Step S306).

Then, the candidate-position extracting circuitry 151 changes the position to (Current=Current+1) and shifts the target to the next frame (Step S307). The candidate-position extracting circuitry 151 determines whether the current frame is an end frame (Step S308). When it is determined that the current frame is the end frame (Yes at Step S308), the candidate-position extracting circuitry 151 ends the processing in the future direction. Meanwhile, when it is determined that the current frame is not the end frame (No at Step S308), the candidate-position extracting circuitry 151 returns to Step S302, and performs the processing on the next frame.

When it is determined that the highest similarity is below the predetermined threshold at Step S305 (Yes at Step S305), the position setting circuitry 152 controls so as to warn a user from the monitor 2 and sets a flag indicating that the information for the region of interest of the frame is not used (Step S309). That is, the position setting circuitry 152 sets the flag in a flag area of the frame as a target of the data illustrated in FIG. 4B. The candidate-position extracting circuitry 151 returns to Step S303, and performs the processing. In the processing in real time, determination of a predetermined range in the next frame can be estimated based on, for example, information for patient's breathing or ECG.

As explained above, according to the first embodiment, the candidate-position extracting circuitry 151 extracts first positions of the region of interest respectively included in the time-series image data collected by performing ultrasonic scanning on the subject injected with the contrast agent based on the similarity of the fundamental wave component between time-series image data. In addition, the candidate-position extracting circuitry 151 extracts second positions of the region of interest respectively included in the time-series image data based on the similarity of the harmonic component between time-series image data. The position setting circuitry 152 sets either one of the first position and the second position as a position of the region of interest for each of the time-series image data, based on the feature of a pixel in the region at the first position and the feature of a pixel in the region at the second position. Therefore, the ultrasonic diagnostic apparatus 100 according to the first embodiment can set a position of the region of interest using information on the side on which the information can be stably obtained from the fundamental image and the harmonic image of each frame in the time series data, and this enables accurate setting of the position of the region of interest. Consequently, the ultrasonic diagnostic apparatus 100 according to the first embodiment uses the region of interest positioned with high accuracy for the TCA, and can thereby improve the accuracy of quantitative analysis.

Moreover, according to the first embodiment, the candidate-position extracting circuitry 151 calculates similarities between a fundamental wave component in the region of interest set in the predetermined image data included in the time-series image data and fundamental wave components in a plurality of candidate regions, each of which has the same size as that of the region of interest, set in an area covering a region at the same position as that of the region of interest set in the time-series image data, and extracts the position of the candidate region with the highest similarity among the calculated ones as the first position. The candidate-position extracting circuitry 151 also calculates similarities between a harmonic component in the region of interest set in the predetermined image data and harmonic components in a plurality of candidate regions, each of which has the same size as that of the region of interest, set in an area covering a region at the same position as that of the region of interest set in the time-series image data, and extracts the position of the candidate region with the highest similarity among the calculated ones as the second position. Therefore, the ultrasonic diagnostic apparatus 100 according to the first embodiment can extract the region of interest with higher accuracy by calculating the similarity for each finely set region in consideration of the change in position of the region of interest.

According to the first embodiment, the position setting circuitry 152 sets the position with a higher similarity as the position of the region of interest, of the similarity between the fundamental wave components at the first position and the similarity between the harmonic components at the second position. Therefore, the ultrasonic diagnostic apparatus 100 according to the first embodiment can set the region of interest with higher accuracy.

According to the first embodiment, the position setting circuitry 152 sets the first position or the second position as a position of the region of interest on condition that a variance value of the pixel value in the region at the first position or at the second position exceeds the predetermined threshold. Therefore, the ultrasonic diagnostic apparatus 100 according to the first embodiment can set a region in which a target site is clearly visualized in the region, as the region of interest. For example, in the harmonic image, when the entire region is dark or when the entire region is shining, it is possible to prevent setting of the region as the region of interest because of the conditions even if the degree of similarity is high.

According to the first embodiment, the candidate-position extracting circuitry 151 extracts the first positions respectively in the normal order and the reverse order of the time series based on the image data where the region of interest is set. The candidate-position extracting circuitry 151 extracts the second positions respectively in the normal order and the reverse order of the time series based on the image data where the region of interest is set. Therefore, the ultrasonic diagnostic apparatus 100 according to the first embodiment can respond to a case where the region of interest is set at any position in the time-series image data. In other words, the region of interest being most easily visible (easily determined) by the observer can be selected freely from any one of the frames in the time series data.

According to the first embodiment, the position setting circuitry 152 sets the first position or the second position as the position of the region of interest on condition that the similarity of the fundamental wave components at the first position or the similarity of the harmonic components at the second position exceeds the predetermined threshold. Therefore, the ultrasonic diagnostic apparatus 100 according to the first embodiment can detect an irregular movement of the position, and can therefore point out an error in operation of the ultrasonic probe, or the like.

According to the first embodiment, when it is determined that the similarity of the fundamental wave components at the first position or the similarity of the harmonic components at the second position does not exceed the predetermined threshold, the position setting circuitry 152 notifies the operator of a warning. Therefore, the ultrasonic diagnostic apparatus 100 according to the first embodiment can immediately respond to the case where an irregular event occurs.

Second Embodiment

Although the first embodiment has been explained so far, various different embodiments other than the first embodiment may be performed.

Figure 9:
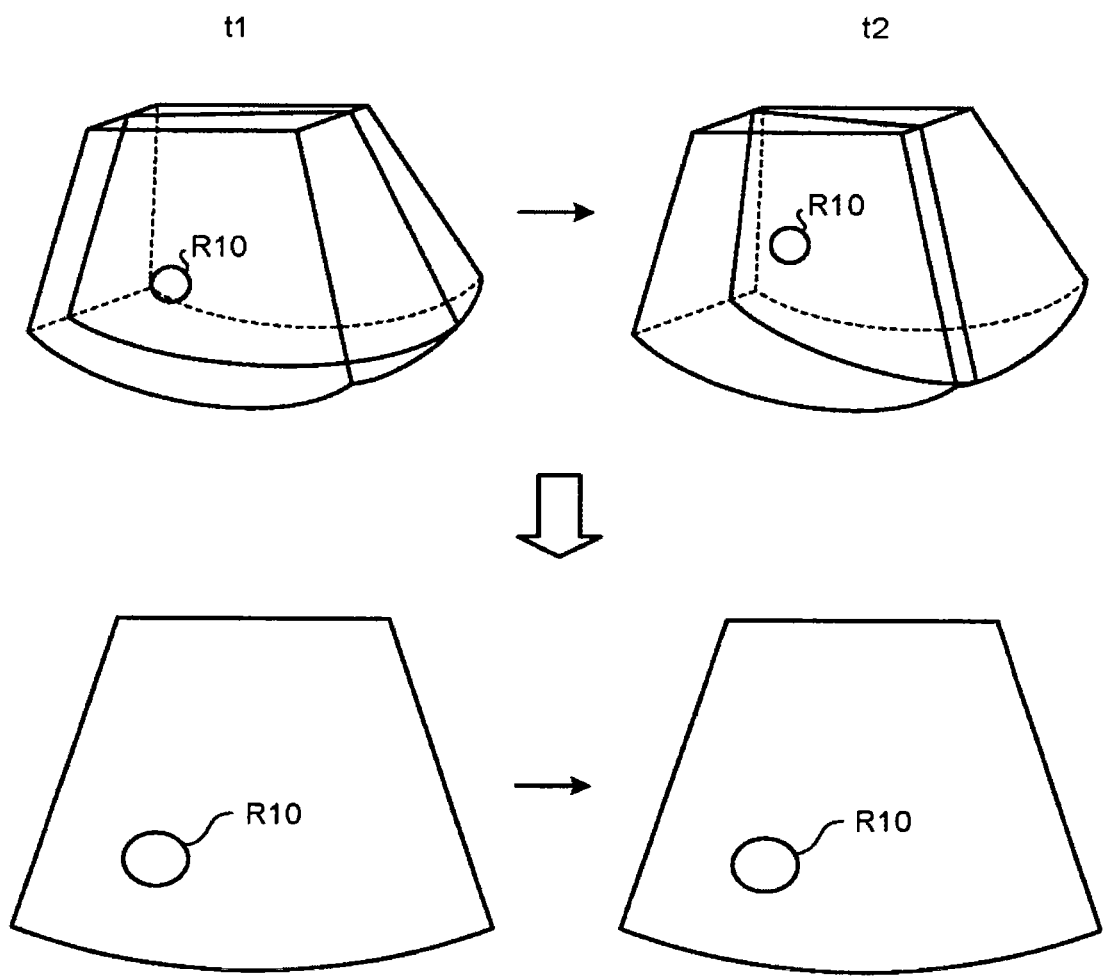
FIG. 9 is a diagram for explaining an example of a case where an ultrasonic diagnostic apparatus according to a second embodiment uses three-dimensional time series data.

The first embodiment has explained the case of using the two-dimensional time series data. However, the embodiment is not limited thereto and, for example, it may be a case of using three-dimensional time series data. FIG. 9 is a diagram for explaining an example of a case where the ultrasonic diagnostic apparatus 100 according to a second embodiment uses three-dimensional time series data. FIG. 9 represents volume data collected at a time of t1 and volume data collected at a time of t2.

For example, when a region of interest R10 is set in the volume data at the time of t1, the candidate-position extracting circuitry 151 according to the second embodiment acquires information for a position of the region of interest R10 and offset. In FIG. 9, because of three-dimensional data, the center coordinates of the region of interest R10 and the offset become (x, y, z) three-axial information. The candidate-position extracting circuitry 151 extracts respective candidate positions of the region of interest R10 in fundamental data and harmonic data of the volume data at t2.

That is, the candidate-position extracting circuitry 151 sets a predetermined three-dimensional region in the fundamental data based on the position of the region of interest R10 at t1 and information for offset, breathing, the state of cardiac phase, and the like, and calculates similarity between each of a plurality of regions in these range and the region of interest R10. The candidate-position extracting circuitry 151 also performs the above processing on the harmonic data.

For example, as illustrated in FIG. 9, the position setting circuitry 152 according to the second embodiment sets a region with the highest similarity as the region of interest R10 at t2 in areas of the fundamental data and the harmonic data. For example, when the change in the position of the region of interest R10 illustrated at t1 to t2 is caused by beating of heart and is a movement in one heartbeat, the position setting circuitry 152 collects three-dimensional ultrasonic image by first one heartbeat, and acquires the position of the region of interest R10 at the time of t2. Therefore, even when two-dimensional ultrasonic image is collected, for example, from second heartbeat, the position setting circuitry 152 changes a scanned cross section to the side of the region of interest and collects it, as illustrated in the upper right figure in FIG. 9, from the information for the position of the region of interest R10 acquired in the cardiac phase at the time of t2, and can thereby collect the region of interest R10 without deviation thereof. In other words, as illustrated in the lower figures in FIG. 9, the observer can observe the ultrasonic image without feeling at all the influence of changes in the position of the region of interest R10.

The first embodiment has explained the case where the candidate positions of the region of interest are respectively extracted from the fundamental image and the harmonic image and either one of the positions of the region of interest is set based on the similarity. However, the embodiment is not limited thereto and, for example, it may be a case where only the fundamental image is used to set the position of the region of interest. In this case, the transmitting/receiving circuitry 11 performs ultrasonic scanning on the subject injected with the contrast agent and collects a plurality pieces of image data. The candidate-position extracting circuitry 151 compares fundamental wave components between the pieces of image data collected by the transmitting/receiving circuitry 11 and extracts a position of the region of interest where predetermined analysis is performed in at least one image data of the pieces of image data.

For example, the transmitting/receiving circuitry 11 performs the ultrasonic scanning on the subject injected with the contrast agent and collects the time-series image data. The candidate-position extracting circuitry 151 extracts positions of the region of interest included in respective time-series image data collected by the transmitting/receiving circuitry 11, based on the similarity of the fundamental wave component between the time-series image data. The position setting circuitry 152 sets the position of the region of interest extracted by the candidate-position extracting circuitry 151, as the position of the region of interest in each of the time-series image data. In other words, the candidate-position extracting circuitry 151 compares the fundamental wave component in the region set in the predetermined position in the predetermined image data included in the pieces of image data and fundamental wave components in a plurality of regions set in a plurality of positions corresponding to a predetermined position in another image data different from the predetermined image data included in the pieces of image data, and extracts the position from the regions, as the position of the region of interest, corresponding to the region having the fundamental wave component most similar to the fundamental wave component in the region set in the predetermined position in the predetermined image data. Thus, it is possible to perform the processing at higher speed than that of the case where a comparison is made using both the fundamental image and the harmonic image. Even if it becomes difficult to specify the region of interest in conventional harmonic image because the fundamental image is used, the region of interest can be set with high accuracy.

The first embodiment has explained the case where an area covering a region at the same position as that of the region of interest set in the predetermined image data is set in another image data of the pieces of image data, and the region of interest is set in the another image data based on the fundamental wave component or the harmonic component in a predetermined region of the predetermined image data. However, the embodiment is not limited thereto and, for example, it may be a case where the region of interest is extracted from the whole region of the another image data and the extracted region of interest is set.

One example will be explained with reference to FIG. 3A and FIG. 3B. For example, the case where the region of interest R1 is set in the frame 3 and the region of interest is set in the frame 2 based on the set region of interest R1 is explained. In this case, when the region of interest R1 is set in the frame 3 of FIG. 3A, the candidate-position extracting circuitry 151 extracts a region with the highest similarity, in the fundamental image of the frame 2, to the region of interest R1 in the fundamental image of the frame 3. For example, the candidate-position extracting circuitry 151 acquires the size (e.g., diameter) of the region of interest R1 set in the frame 3. The candidate-position extracting circuitry 151 then extracts a region of the same size as the size acquired from the fundamental image of the frame 2, and calculates the similarity between the extracted region and the region of interest R1. Here, the candidate-position extracting circuitry 151 extracts regions each with the same size as that of the region of interest R1 from the whole region of the fundamental image of the frame 2 while shifting the pixels one by one, and calculates the similarity between each of the extracted regions and the region of interest R1. In this manner, the candidate-position extracting circuitry 151 calculates similarities between all the regions extracted from the frame 2 and the region of interest R1, and extracts the region with the highest similarity as a candidate position of the region of interest in the fundamental image of the frame 2.

Likewise, the candidate-position extracting circuitry 151 extracts the region with the highest similarity, in the harmonic image of the frame 2, to the region of interest R1 in the harmonic image of the frame 3. For example, the candidate-position extracting circuitry 151 extracts regions each with the same size as that of the region of interest R1 from the whole region of the harmonic image of the frame 2 while shifting the pixels one by one, and calculates the similarity between each of the extracted regions and the region of interest R1 in the harmonic image of the frame 3. The candidate-position extracting circuitry 151 then extracts the region with the highest similarity as a candidate position of the region of interest in the harmonic image of the frame 2. The position setting circuitry 152 sets the position with a higher similarity, as the region of interest of the frame 2, of the candidate positions in the fundamental image and the candidate positions in the harmonic image which are extracted by the candidate-position extracting circuitry 151. The example has explained the case where the candidate positions of the regions of interest are respectively extracted from the fundamental image and from the harmonic image and the candidate position with a higher similarity is set as the region of interest. However, the embodiment is not limited thereto, and it may be a case where the candidate position extracted from either one of the fundamental image and the harmonic image is set as the region of interest without any change.

The first embodiment has explained the case of setting the region of interest in the same time series data. However, the embodiment is not limited thereto and, for example, it may be a case of setting the region of interest in data whose collection period is different. For example, when the follow-up is performed after treatment of the same patient, it may be a case of setting the region of interest of the current data based on the region of interest set in the past. In this case, for example, the candidate-position extracting circuitry 151 acquires information for the position of the region of interest set in the past (e.g., coordinates of the center) and the size (e.g., diameter) thereof. The candidate-position extracting circuitry 151 sets a plurality of sub-regions each with the same size as the region of interest in an area covering the same position as the position of the region of interest set in the past, based on the acquired information.

The candidate-position extracting circuitry 151 calculates the similarities between the set sub-regions and the region of interest set in the past, and extracts the sub-region with the highest similarity. For the extraction of the sub-region with the highest similarity, it may be the case where sub-regions are extracted respectively from the fundamental image and the harmonic image and the position with a higher similarity is set as the position of the region of interest. However, when the follow-up after the treatment is performed, it may be a case where the position of the sub-region with the highest similarity extracted from the fundamental image is set as the position of the region of interest without any change because there is sometimes a case where the temporal change of the contrast agent may be significantly changed due to the treatment.

In this way, the ultrasonic diagnostic apparatus 100 according to the present application can set a region of interest in a predetermined frame included in current data based on the region of interest set in a predetermined frame included in previous data. Furthermore, when the region of interest is set in the predetermined frame included in the current data, the ultrasonic diagnostic apparatus 100 according to the present application further sets a region of interest in another frame included in the current data based on the set region of interest. However, it may be also a case where any one of the frames included in the previous data is used for the previous frame to acquire the information for the region of interest.

The example has explained the case where a plurality of sub-regions are set in an area covering the same position as that of the region of interest set in the previous frame and the similarities are compared. However, the embodiment is not limited thereto and, for example, it may be a case where candidate positions are extracted from the whole area of the current frame and the region of interest is set. In other words, because the regions of interest are set between image data whose collection periods are different, the candidate positions may be extracted from the whole area in consideration of deviation or so between the data.

The first embodiment has explained the case where the ultrasonic diagnostic apparatus 100 sets the region of interest in the time series data. However, the embodiment is not limited thereto and, for example, it may be a case where the image processing apparatus sets the region of interest in the time series data. In this case, for example, the image processing apparatus extracts the first positions of the region of interest respectively included in the time-series image data collected by performing ultrasonic scanning on the subject injected with the contrast agent, based on the similarity of the fundamental wave component between the time-series image data. The image processing apparatus extracts the second positions of the region of interest respectively included in the time-series image data, based on the similarity of the harmonic component between the time-series image data. The image processing apparatus then sets either one of the first position and the second position as the position of the region of interest in the time-series image data respectively, based on the feature of a pixel in the region at the first position and the feature of a pixel in the region at the second position.

The configuration of the ultrasonic diagnostic apparatus 100 according to the first embodiment is only an example, and therefore integration and separation of the respective circuitry can be appropriately performed. For example, the candidate-position extracting circuitry 151 and the position setting circuitry 152 can be integrated. Further, the B-mode processing circuitry 12, the Doppler processing circuitry 13, the image generating circuitry 14, image processing circuitry 15 and the control circuitry 18 can be integrated appropriately. In addition, for example, the candidate-position extracting circuitry 151 can be separated into first extracting circuitry that extracts a candidate position from the fundamental image and second extracting circuitry that extracts a candidate position from the harmonic image.

The functions of the candidate-position extracting circuitry 151 and the position setting circuitry 152 explained in the first embodiment can also be implemented by software. For example, the functions of the candidate-position extracting circuitry 151 and the position setting circuitry 152 are implemented by causing a computer to execute an image processing program defining the procedures of processing having been explained as these performed by the candidate-position extracting circuitry 151 and the position setting circuitry 152 in the embodiment. The image processing program is stored in a hard disk, a semiconductor memory device, or the like, and is executed by being read by a processor such as CPU and MPU. The image processing program can be distributed by being recorded in a computer-readable recording medium such as CD-ROM (Compact Disc-Read Only Memory), MO (Magnetic Optical disk), and DVD (Digital Versatile Disc).

As explained above, according to the present embodiment, it becomes possible to improve the accuracy of quantitative analysis by the contrast echo method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
processing circuitry configured to
control a probe to perform ultrasonic scanning on a subject injected with contrast agent to generate a plurality of pieces of reflected wave data in time series,
generate, in accordance with the plurality of pieces of reflected wave data in time series, a plurality of pieces of fundamental wave data in time series in which tissue in the subject functions as a reflection source and a plurality of pieces of harmonic data in time series in which microbubbles included in the contrast agent function as a reflection source,
generate a plurality of fundamental images based on the plurality of pieces of fundamental wave data in time series and a plurality of harmonic images based on the plurality of pieces of harmonic data in time series,
set, in accordance with a position of a first region of interest in a fundamental image of a first time phase among the plurality of fundamental images, a plurality of sub regions in a fundamental image of a second time phase among the plurality of fundamental images,
compare the first region of interest in the fundamental image of the first time phase with each of the plurality of sub regions in the fundamental image of the second time phase, respectively, and extract a sub region of the plurality of sub regions in the fundamental image, as a first candidate position for a second region of interest in an ultrasonic image based on reflected wave data of the second time phase among the plurality of pieces of reflected wave data,
set, in accordance with a position of a first region of interest in a harmonic image of the first time phase among the plurality of harmonic images, a plurality of sub regions in a harmonic image of the second time phase among the plurality of harmonic images,
compare the first region of interest in the harmonic image of the first time phase with each of the plurality of sub regions in the harmonic image of the second time phase, respectively, and extract a sub region of the plurality of sub regions in the harmonic image, as a second candidate position for the second region of interest in the ultrasonic image based on reflected wave data of the second time phase among the plurality of pieces of reflected wave data,
compare a first similarity between the sub region corresponding to the first candidate position and the first region of interest in the fundamental image with a second similarity between the sub region corresponding to the second candidate position and the first region of interest in the harmonic image, and
set the sub region having a higher similarity between the first similarity and the second similarity, as the second region of interest in the ultrasonic image of the second dine phase, wherein
the second region of interest is an analysis region in which Time Curve Analysis (TCA) relating to administration of the contrast agent is performed.

2. The ultrasonic diagnostic apparatus according to claim 1, wherein the processing circuitry is configured to
compare a pixel value in the first region of interest in the fundamental image of the first time phase and each pixel value of the plurality of sub regions in the fundamental image of the second time phase, respectively, and extract, as the first candidate position, the sub region having a pixel value most similar to the pixel value in the first region of interest in the fundamental image of the first time phase, and
compare a pixel value in the first region of interest in the harmonic image of the first time phase and each pixel value of the plurality of sub regions in the harmonic image of the second time phase, respectively, and extract, as the second candidate position, the sub region having a pixel value most similar to the pixel value in the first region of interest in the harmonic image of the first time phase.

3. The ultrasonic diagnostic apparatus according to claim 1, wherein the processing circuitry is configured to set the sub region having the higher similarity between the first similarity and the second similarity as the second region of interest on condition that a variance value of pixel values of a plurality of pixels included in the sub region exceeds a predetermined threshold.

4. The ultrasonic diagnostic apparatus according to claim 1, wherein the processing circuitry is configured to
extract the sub region corresponding to the first candidate position in each of a fundamental image of a time phase among the plurality of fundamental images in chronological order and a fundamental image of a time phase among the plurality of fundamental images in reverse chronological order based on the fundamental image of the first time phase where the first region of interest is set, and
extract the sub region corresponding to the second candidate position in each of a harmonic image of a time phase among the plurality of harmonic images in the chronological order and a harmonic image of a time phase among the plurality of harmonic images in the reverse chronological order based on the harmonic image of the first time phase where the first region of interest is set.

5. The ultrasonic diagnostic apparatus according to claim 1, wherein the processing circuitry is configured to set the sub region as the second region of interest on condition that the higher similarity exceeds a predetermined threshold.

6. The ultrasonic diagnostic apparatus according to claim 5, wherein the processing circuitry is further configured to notify an operator of a warning when the first similarity based on a pixel value in the sub region corresponding to the first candidate position and the second similarity based on a pixel value in the sub region corresponding to the second candidate position are determined to not exceed the predetermined threshold.

7. The ultrasonic diagnostic apparatus according to claim 1, wherein the second region of interest set in the ultrasonic image of the second time phase has a same shape and a same size as the first region of interest in the fundamental image of the first time phase and the first region of interest in the harmonic image of the first time phase.

8. An image processing apparatus comprising:
processing circuitry configured to
acquire a plurality of fundamental images based on a plurality of pieces of fundamental wave data in time series in which tissue in a subject functions as a reflection source in a plurality of pieces of reflected wave data in time series,
acquire a plurality of harmonic images based on a plurality of pieces of harmonic data in time series in which microbubbles included in a contrast agent function as a reflection source in the plurality of pieces of reflected wave data in time series,
set, in accordance with a position of a first region of interest in a fundamental image of a first time phase among the plurality of fundamental images, a plurality of sub regions in a fundamental image of a second time phase among the plurality of fundamental images,
compare the first region of interest in the fundamental image of the first time phase with each of the plurality of sub regions in the fundamental image of the second time phase, respectively, and extract a sub region of the plurality of sub regions in the fundamental image, as a first candidate position for a second region of interest in an ultrasonic image based on reflected wave data of the second time phase among the plurality of pieces of reflected wave data,
set, in accordance with a position of a first region of interest in a harmonic image of the first time phase among the plurality of harmonic images, a plurality of sub regions in a harmonic image of the second time phase among the plurality of harmonic images,
compare the first region of interest in the harmonic image of the first time phase with each of the plurality of sub regions in the harmonic, image of the second time phase, respectively, and extract a sub region of the plurality of sub regions in the harmonic image, as a second candidate position for the second region of interest in the ultrasonic image based on reflected wave data of the second time phase among the plurality of pieces of reflected wave data,
compare a first similarity between the sub region corresponding to the first candidate position and the first region of interest in the fundamental image with a second similarity between the sub region corresponding to the second candidate position and the first region of interest in the harmonic image, and
set the sub region having a higher similarity between the first similarity and the second similarity, as the second region of interest in the ultrasonic image of the second time phase, wherein
the second region of interest is an analysis region in which Time Curve Analysis (TCA) relating to administration of the contrast agent is performed.

9. The image processing apparatus according to claim 8, wherein the second region of interest set in the ultrasonic image of the second time phase has a same shape and a same size as the first region of interest in the fundamental image of the first time phase and the first region of interest in the harmonic image of the first time phase.

* * * * *